United States Patent
Bynum

(10) Patent No.: US 11,850,368 B2
(45) Date of Patent: Dec. 26, 2023

(54) MODULAR FIDGET DEVICE FOR HEIGHTENED MENTAL STIMULATION VIA CREATIVE CUSTOMIZATION AND SKILL-BASED PLAY

(71) Applicant: David K. Bynum, Portland, OR (US)

(72) Inventor: David K. Bynum, Portland, OR (US)

( * ) Notice: Subject to any disclaimer, the term of this patent is extended or adjusted under 35 U.S.C. 154(b) by 0 days.

(21) Appl. No.: 18/130,993

(22) Filed: Apr. 5, 2023

(65) Prior Publication Data
US 2023/0321391 A1 Oct. 12, 2023

Related U.S. Application Data

(60) Provisional application No. 63/327,817, filed on Apr. 6, 2022.

(51) Int. Cl.
| | | |
|---|---|---|
| *A61M 21/02* | (2006.01) | |
| *A63H 33/00* | (2006.01) | |
| *A61M 21/00* | (2006.01) | |

(52) U.S. Cl.
CPC .............. *A61M 21/02* (2013.01); *A63H 33/00* (2013.01); *A61M 2021/0022* (2013.01)

(58) Field of Classification Search
None
See application file for complete search history.

(56) References Cited

U.S. PATENT DOCUMENTS

| | | | |
|---|---|---|---|
| 5,346,418 A | 9/1994 | Arad | |
| 8,316,492 B2 | 11/2012 | Barber | |
| 8,393,069 B2 | 3/2013 | Glesser | |
| 8,764,213 B2 | 7/2014 | Cammenga | |
| 8,870,486 B2 | 10/2014 | Castro | |
| 8,998,674 B2 | 4/2015 | Richins | |
| 10,836,028 B2 | 11/2020 | Saito | |
| 10,948,177 B1 | 3/2021 | Mowry | |
| 2006/0087845 A1 | 4/2006 | Yeh | |
| 2009/0149698 A1* | 6/2009 | Tastard | A61M 21/00 472/133 |
| 2012/0017442 A1 | 1/2012 | King | |
| 2014/0154945 A1 | 6/2014 | Labarbara | |
| 2018/0193764 A1 | 7/2018 | Sparger | |
| 2018/0332155 A1 | 11/2018 | Babbage, III | |
| 2019/0083892 A1 | 3/2019 | Howard | |

(Continued)

FOREIGN PATENT DOCUMENTS

| | | | |
|---|---|---|---|
| KR | 200484864 Y1 * | 11/2017 | |
| KR | 200494604 Y1 * | 11/2021 | |

OTHER PUBLICATIONS

"LEGO Butterfly Knife (Balisong)," instructables.com. https://www.instructables.com/LEGO-Butterfly-Knife-Balisong/ [Date accessed: Mar. 11, 2022].

(Continued)

*Primary Examiner* — Thaddeus B Cox
(74) *Attorney, Agent, or Firm* — Bold IP, PLLC

(57) ABSTRACT

A fidget device is disclosed that can be customized with one or more modular components and manipulated by a user to perform a series of tricks. The fidget device includes a center hub that has a pivotal attachment mechanism and a component grip configured to be pivotally attached to the center hub. The component grip comprises a component attachment mechanism configured to attach one or more modular components to the component grip.

19 Claims, 13 Drawing Sheets

(56) References Cited

U.S. PATENT DOCUMENTS

2021/0154867 A1 5/2021 Demko
2021/0379501 A1* 12/2021 Klauber ............... A63H 33/042

OTHER PUBLICATIONS

"Fidget Flipper," etsy.com. https://www.etsy.com/listing/940532198/fidget-flipper?click_key=852568300bd9b8ce040d90d689bb439327c0bd40%3A940532198&click_sum=d1817772&ga_order=most_relevant&ga_search_type=all&ga_view_type=gallery&ga_search_query=fidget+flipper&ref=sr_gallery-1-1&col=1&sts=1 [Date accessed: Mar. 11, 2022].

"Flip Finz Assortment," walmart.com. https://www.walmart.com/ip/Flip-Finz-Assortment/368522520 [Date accessed: Mar. 11, 2022].

* cited by examiner

MODULAR FIDGET DEVICE FOR HEIGHTENED MENTAL STIMULATION VIA CREATIVE CUSTOMIZATION AND SKILL-BASED PLAY

CROSS-REFERENCE TO RELATED APPLICATIONS

This application is a non-provisional application that claims the benefit of priority of U.S. provisional patent application No. 63/327,817, filed on Apr. 6, 2022, which is incorporated by reference in its entirety.

FIELD OF THE DISCLOSURE

This disclosure relates generally to the field of fidget devices, and more particularly to a fidget device that can be customized with one or more modular components and manipulated by a user to perform a series of tricks.

BACKGROUND

A fidget device is a handheld object that is designed to provide sensory stimulation and to help individuals cope with anxiety, stress, or attention-deficit/hyperactivity disorder (ADHD). Fidget devices come in a variety of forms, such as spinners, cubes, balls, and other shapes, and are often made of materials such as plastic, metal, or wood.

Fidget devices can help individuals redirect their excess energy or nervousness into a physical activity, which can promote a sense of calmness and focus. For example, spinning a fidget spinner or rolling a fidget ball in your hand can be a way to relieve stress or anxiety. Fidget devices have become popular in recent years, particularly among students and office workers who may find them helpful during periods of intense concentration or stress.

Most fidget devices offer a static selection of fidget components that do not allow users to customize or reconfigure functional, tactile, and aesthetic components of the fidget device to their liking. This prescribed selection and orientation of fidget components reduces the scope of play and the longevity of the fidget device. There is a need for a fidget device that has a modular building platform and a dynamic, wide, and varied selection of fidget components.

Furthermore, many fidget devices focus on short term mental stimulation involving repetitive actions and lack a skill-based kinesthetic component that could further enhance mental and physical dexterity as the user acquires more skill. The addition of a skill-based play component offers more long-term value to a user by incorporating an inherent learning curve whereby play becomes more advanced and nuanced with continued use.

SUMMARY

This disclosure provides a handheld skill-based fidget device that allows for visual, tactile, and functional customization to provide a personalized fidgeting experience. The fidget device enhances mental stimulation via a configurable fidget platform and improves physical dexterity through an interactive skill-based play component that encourages the user to learn tricks that extend the device's functionality. The quality of life for those seeking a fun and stimulating fidgeting experience can be improved by the teachings of this disclosure.

Multiple levels of interactivity, sensory immersion, and stimulation are provided by the fidget device of this disclosure, which can be very helpful for those suffering from ADHD. Aesthetic stimulation is provided, whereby the various color, textures, and shapes of the fidget device components come together to create the impression of a unified product that is greater than the sum of its component parts (similar to dressing up a doll). Functional stimulation is provided, whereby use and capability of the fidget device changes depending on the sum configuration of parts. Fidget-based stimulation is provided, whereby the fidget device may be customized and configured with any number of modular fidget components to provide a whole new level of interactivity. Skill-based stimulation is provided, whereby use of the fidget device involves an inherent learning curve and play becomes more advanced and nuanced with continued use (similar to the manner in which the use of a yoyo or a skateboard is extended via tricks).

One aspect of this disclosure is a fidget device comprising a center hub that has a pivotal attachment mechanism and a component grip configured to be pivotally attached to the center hub. The component grip comprises a component attachment mechanism configured to attach one or more modular components to the component grip.

In one implementation, the component attachment mechanism comprises a component rail configured to slidably receive the one or more modular components and a retaining mechanism configured to retain the one or more modular components on the component rail. In this implementation, the component rail may be an inverted T-slot track, and the retaining mechanism may be a spring-loaded lever.

In a further implementation, the component attachment mechanism comprises one or more apertures configured to receive corresponding protrusions formed on the one or more modular components. In this implementation, the one or modular components may comprise faceplates.

In a further implementation, the fidget device comprises two component grips that are configured to be pivotally attached to the center hub.

In a further implementation, the pivotal attachment mechanism comprises a socket formed in the center hub that is configured to receive a corresponding protrusion formed on the component grip.

In a further implementation, the center hub comprises an endpiece attachment mechanism formed at an end of the center hub opposite from the pivotal attachment mechanism. In this implementation, the endpiece attachment mechanism may be a hub connector with a reduced diameter relative to a remainder of the center hub and that is configured to retain an endpiece thereon that alters the perceived nature and utility of the fidget device.

In a further implementation, the center hub is hollow and defines a battery compartment for receiving and holding a battery. In this implementation, the endpiece attachment mechanism may be configured to provide an electrical connection between the center hub and an endpiece connected to the endpiece attachment mechanism.

In a further implementation, the fidget device comprises an actuation device that is configured to control at least one function of the fidget device. In this implementation, the actuation device may be a button configured to supply power to the fidget device.

In a further implementation, the center hub houses a near field communication (NFC) chip. The center hub may also house an inertial measurement unit (IMU).

In a further implementation, the component grip comprises a recess that acts as a protective shroud for the center hub.

In a further implementation, the component grips are configured with positive and negative contacts and appropriate conductors to supply power and/or data from the center hub to modular components that require power and/or data to operate.

In a further implementation, the fidget device has a sensor that allows movement of the fidget device to be tracked in real time. In this implementation, the sensor may orient a 3D position of the fidget device to enable a visual representation in 3D digital space of the fidget device.

Other aspects and advantages will be apparent from the following description and appended claims.

BRIEF DESCRIPTION OF THE DRAWINGS

Embodiments of the invention are described in detail below with reference to the following drawings. The drawings are for illustrative purposes only, do not show all possible embodiments, and are not intended to limit the scope of this description.

DETAILED DESCRIPTION

This disclosure is directed to a modular fidget device that is operated by a user's hand, wherein the user may interact with the fidget device in numerous ways such as by interacting with attached fidget components, or by doing tricks with the fidget device, such as flipping, spinning, or catching tricks.

Figure 1:
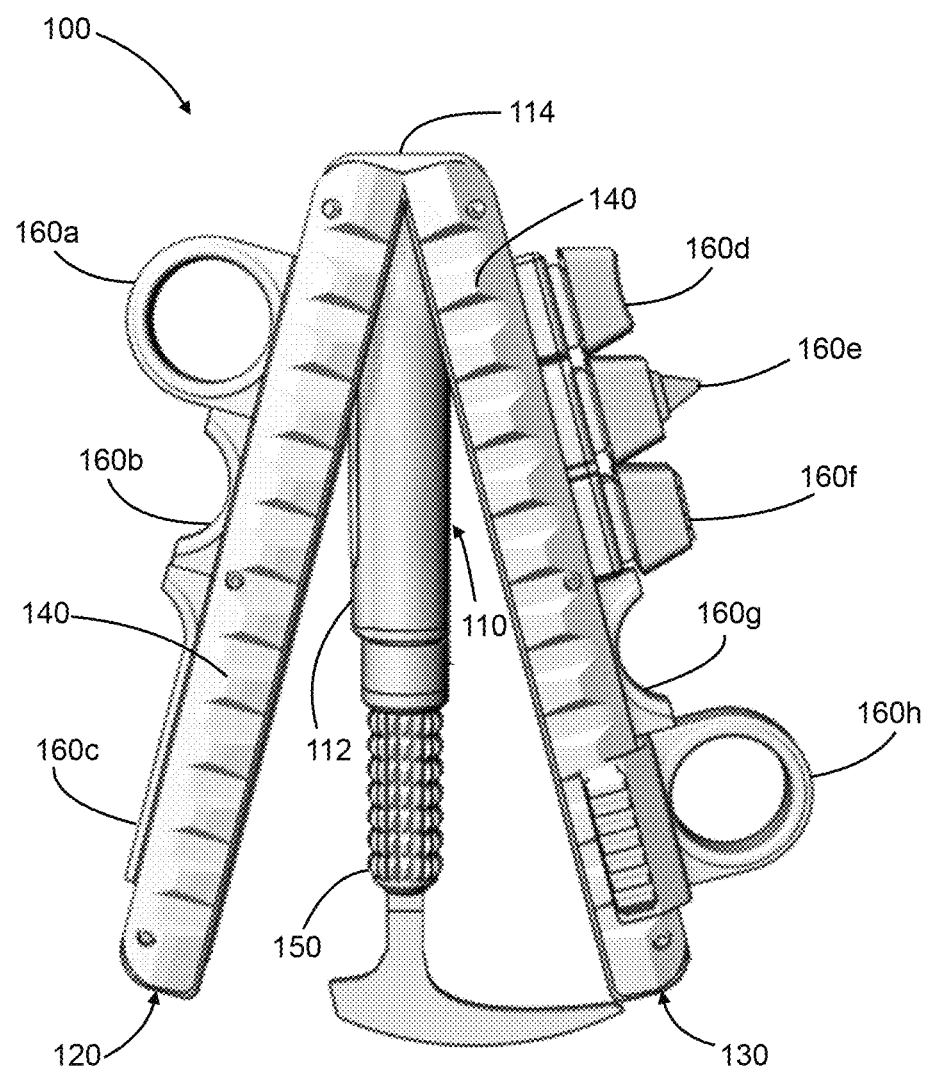
FIG. 1 is a side view of one embodiment of a fidget device in an open configuration, according to this disclosure.
Figure 2:
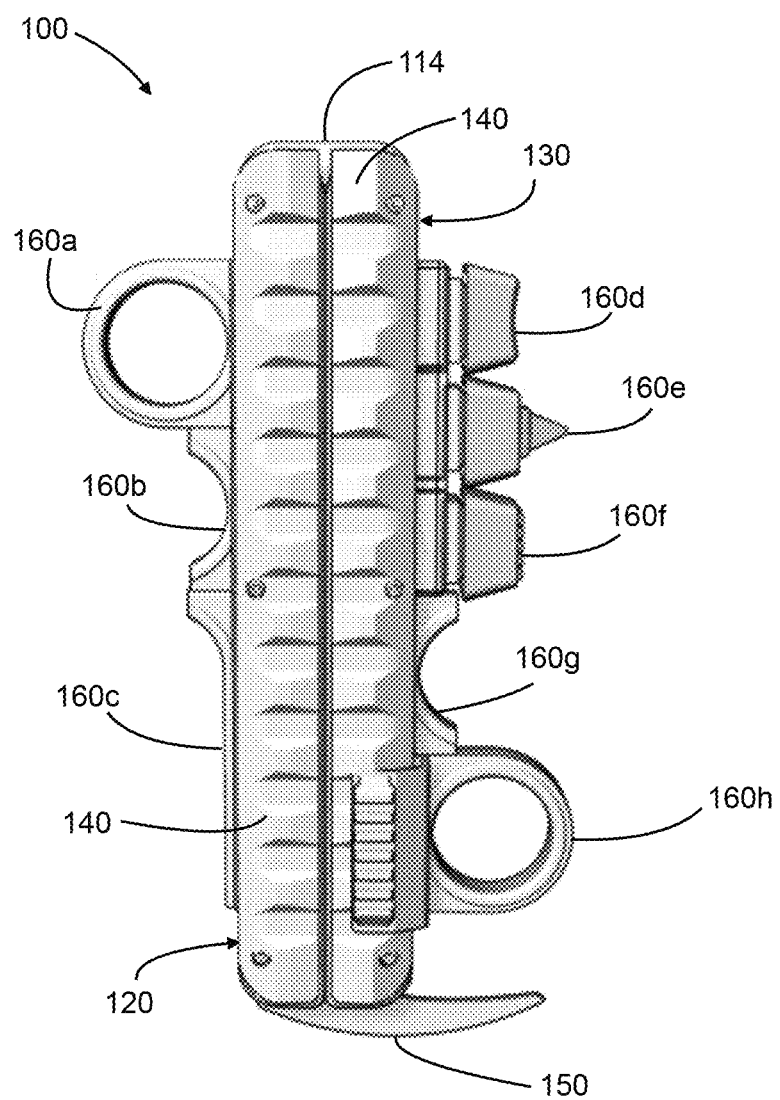
FIG. 2 is a side view of the fidget device in a closed configuration, according to this disclosure.

FIGS. 1 and 2 are side views of a fidget device 100 in respective open and closed configurations. Fidget device 100 may also be referred to herein as an interactive apparatus. Fidget device 100 comprises a center hub 110 that acts as the core of device 100, and at least one component grip (or handle) configured to be pivotally attached to center hub 110. In one non-limiting example, a dual component grip configuration is provided in which a first component grip 120 and a second component grip 130 are pivotally attached to center hub 110. As will be described below, center hub 110 and component grips 120, 130 are configured with component attachment mechanisms permitting attachment of various modular components, such as modular components 160a ... 160h. Fidget device 100 is operated by a user grasping one or both of component grips 120, 130 and/or manipulating or operating one or more of modular components 160a ... 160h.

Figure 8:
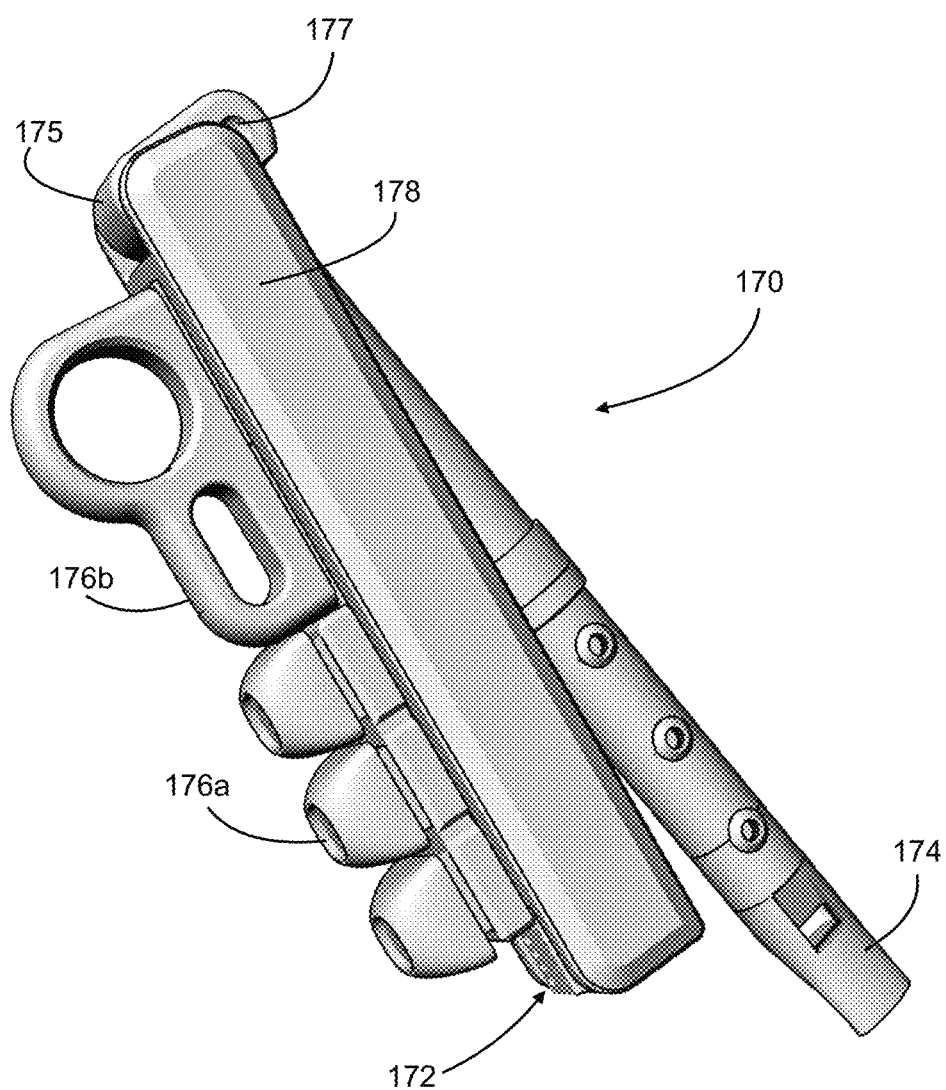
FIG. 8 is a perspective view of a fidget device configured in a single component grip configuration including one component grip, according to this disclosure.

In the illustrated dual component grip configuration, fidget device 100 takes on a form similar to that of a balisong, which is a type of folding knife that is characterized by two handles that rotate around a blade pivot. The handles of a balisong are designed to be flipped open with a single hand, which makes it a popular choice among knife enthusiasts who practice flipping tricks. Although this description focuses primarily on a dual component grip configuration, the fidget device may also be configured in a single component grip configuration 170 in which the device includes just one component grip 172 (FIG. 8).

Figure 3:
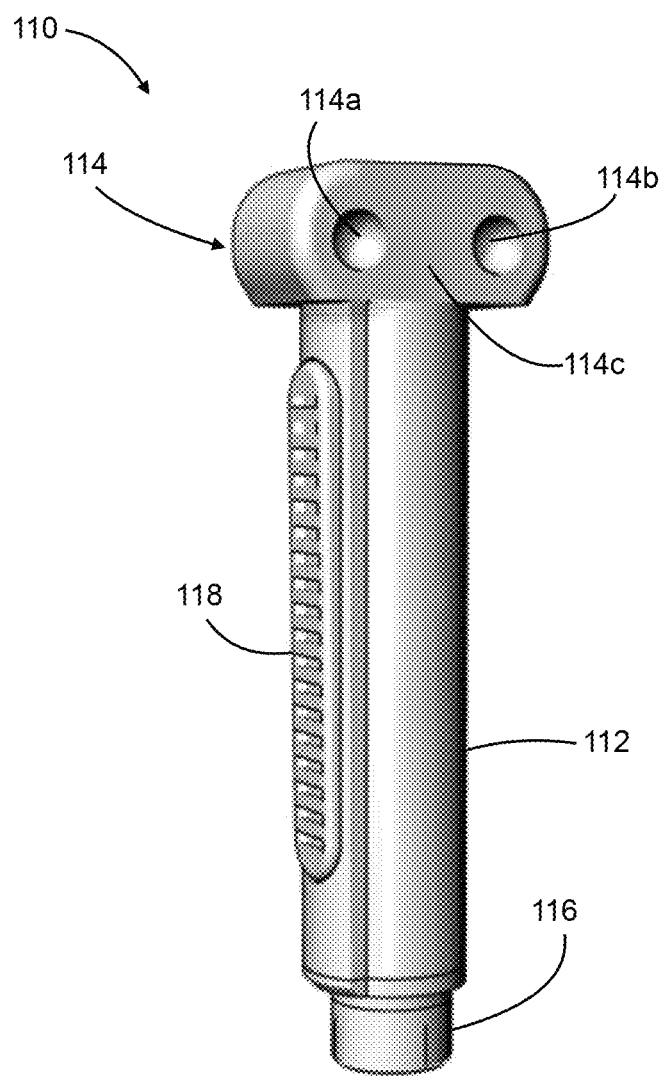
FIG. 3 is a perspective view of a center hub of the fidget device, according to this disclosure.

Referring to FIG. 3, center hub 110 comprises hub body 112 extending between base 114 formed at one end of hub body 112 and endpiece attachment mechanism 116 formed at an opposite end of hub body 112. In one non-limiting example, endpiece attachment mechanism 116 is a hub connector to which an endpiece 150 is attached. Hub connector 116 may have a reduced diameter relative to hub body 112, such that endpiece 150 fits around and onto hub connector 116 with a frictional or interference fit. Endpiece attachment mechanism 116 may be alternatively configured, for example, it may have a screw on/twist lock design.

Figure 6:
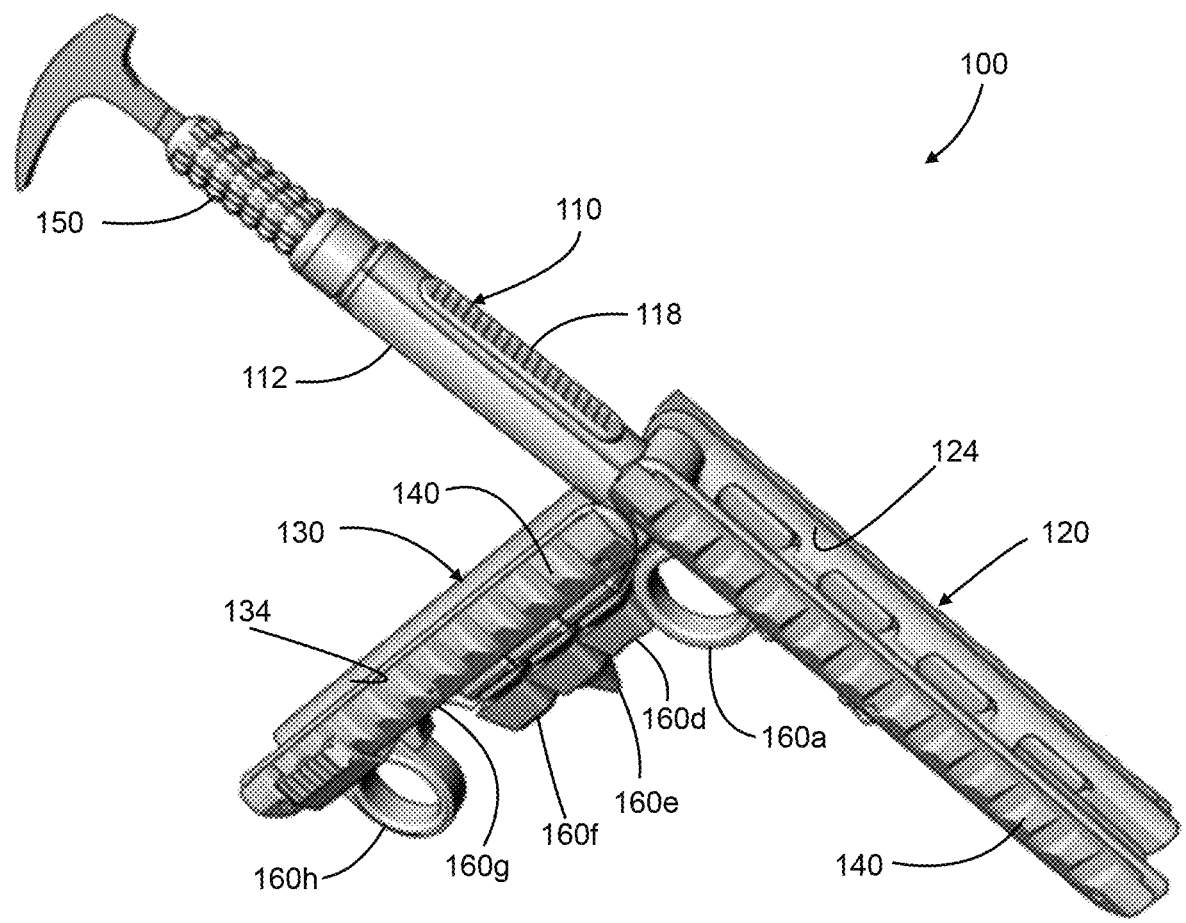
FIG. 6 is a perspective view of the fidget device in an open configuration with an endpiece attached to the center hub, according to this disclosure.
Figure 7:
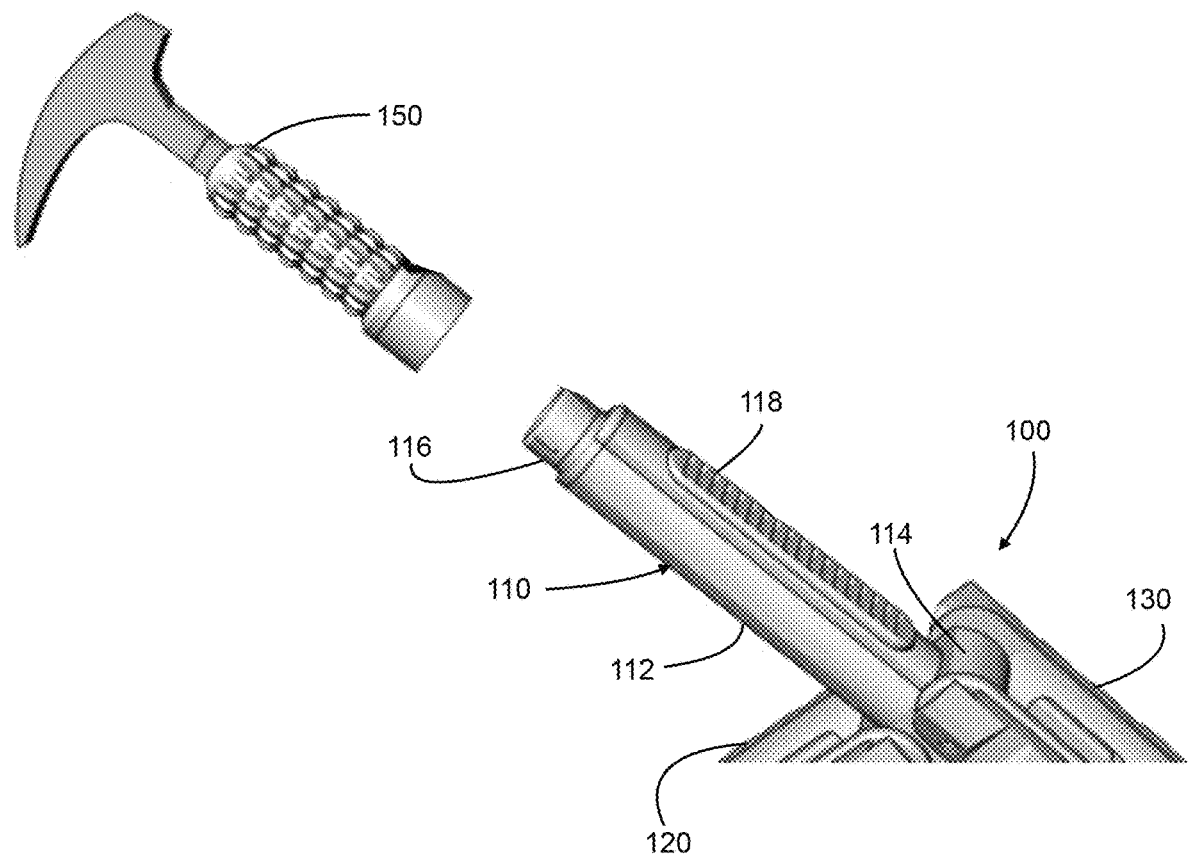
FIG. 7 is an exploded view of the center hub of the fidget device with an endpiece positioned for attachment to the center hub, according to this disclosure.

In one non-limiting example, as shown in FIGS. 1, 2, 6 and 7, endpiece 150 may be a scythe blade attachment. FIGS. 1, 2 and 6 show scythe blade attachment 150 in a state of being attached to hub connector 116, and FIG. 7 shows scythe blade attachment 150 in a state of being detached from hub connector 116. Other non-limiting examples of the virtually unlimited forms that endpiece 150 may take include a marker or other writing instrument, a crochet hook or other functional tool, a wand, a tentacle, a mini recorder whistle, flute, or other musical instrument. The choice of endpiece can significantly alter the perceived nature and utility of fidget device 100. For example, when equipped with two component grips and a flute endpiece, device 100 reads as a balisong flute, whereas when equipped with a single component grip 172 and a flute endpiece 174 (FIG. 8), the device takes on a significantly different appearance.

In one implementation, hub body 112 is hollow and defines a battery compartment for receiving and holding batteries such as a rechargeable lithium-ion battery, or conventionally sized AA or AAA batteries, for example. The battery compartment may include one or more electrodes configured to contact electrically conductive surfaces of the battery received inside the compartment and may be accessible, for example, by operating a cover or latch mechanism that holds and conceals the batteries within hub body 112. Batteries may be provided within hub body 112 to provide power to features of fidget device 100. Alternatively, or in addition, fidget device 100 may be configured to connect to an external charger, such as a USB charger, or to plug into an electrical outlet using an electrical cord.

In addition to a mechanical connection, hub connector 116 may provide an electrical connection between hub body 112 and an endpiece connected to hub connector 116. In one non-limiting example, a thin spring or strip of metal such as copper or brass may be located within hub body 112 and hub connector 116 to electrically connect endpiece 150 or other components of fidget device 100 to a battery contained within hub body 112 or to another power source. Some non-limiting examples of the virtually unlimited form that powered endpieces may take include a lightsaber blade, LED lighting features and tips, soldering iron tips, and a vaporizer.

Center hub 110 may include an actuation device 118 to control power and/or other functions of fidget device 100. Non-limiting examples of actuation device 118 include a button, a touch panel, and a sensor. When a user's hand is positioned on fidget device 100, actuation device 118 may be pressed or otherwise operated by one or more of the user's fingers and thumb. Actuation device 118, when taking the form of a button, may have a spring mechanism or compressible material such that button 118 springs back up when the user releases button 118. Actuation device 118 may alternatively take other suitable forms, such as a touch panel with capacitive sense capabilities whose properties are altered when touched.

In addition to a power source, center hub 110 may also contain internal electronic components such as, but not limited to: a near field communication (NFC) chip, which enables two devices to communicate wirelessly when brought into close proximity; a battery control board; an inertial measurement unit (IMU), which is a sensor system for tracking positional data that typically consists of several sensors such as accelerometers, gyroscopes, and magnetometers; and a wireless module for transmitting data.

Component grips 120, 130 act as the primary point of contact for the user's hand. A pivotal attachment mechanism allows pivotal attachment of component grips 120, 130 to hub base 114 such that component grips 120, 130 can rotate pivotally about center hub 110. In one non-limiting example, the pivotal attachment mechanism comprises hub sockets or apertures 114a, 114b that receive mating protrusions formed on component grips 120, 130. Hub sockets 114a, 114b are formed on face 114c of hub base 114 (FIG. 3), and corresponding hub sockets are formed on a corresponding face (not shown) on an opposite side of hub base 114 relative to face 114c. Alternatively, the pivotal attachment mechanism may be any other suitable configuration that allows component grips 120, 130 to rotate pivotally about center hub 110, such as connection of component grips 120, 130 to center hub 110 via pins.

Figure 5:
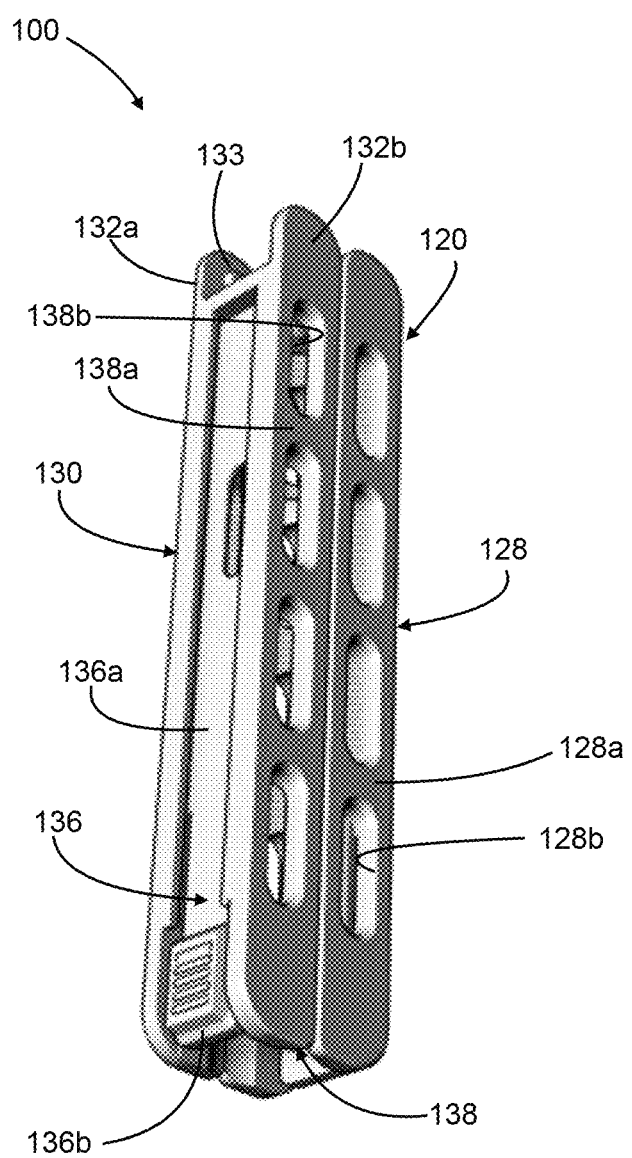
FIG. 5 is a perspective view of the fidget device in a closed configuration and rotated clockwise relative to the view of FIG. 4, according to this disclosure.

In one example, protrusions formed on inside surfaces of prongs 122a, 122b of component grip 120 are received in hub sockets 114a formed in face 114c of hub base 114 and in an opposite face of base 114, and protrusions formed on inside surfaces of prongs 132a, 132b of component grip 130 are received in hub sockets 114b formed in face 114c of hub base 114 and in an opposite face of base 114. One such protrusion 133 on the inside surface of prong 132a is illustrated in FIG. 5. In this manner, component grips 120, 130 can pivotally rotate about center hub 110 in the manner of a ball and socket joint. The protrusions formed on component grips 120, 130 snap into place in hub sockets 114a, 114b, such that once installed, they remain substantially in place until a sufficient force is used to remove the protrusions from hub sockets 114a, 114b.

Referring to FIG. 5, when in a closed position, component grips 120, 130 act as a protective shroud for center hub 110 and any attached endpiece, with center hub 110 being contained within recesses 124, 134 (see FIGS. 4 and 6) formed on respective inner sides of component grips 120, 130.

Figure 4:
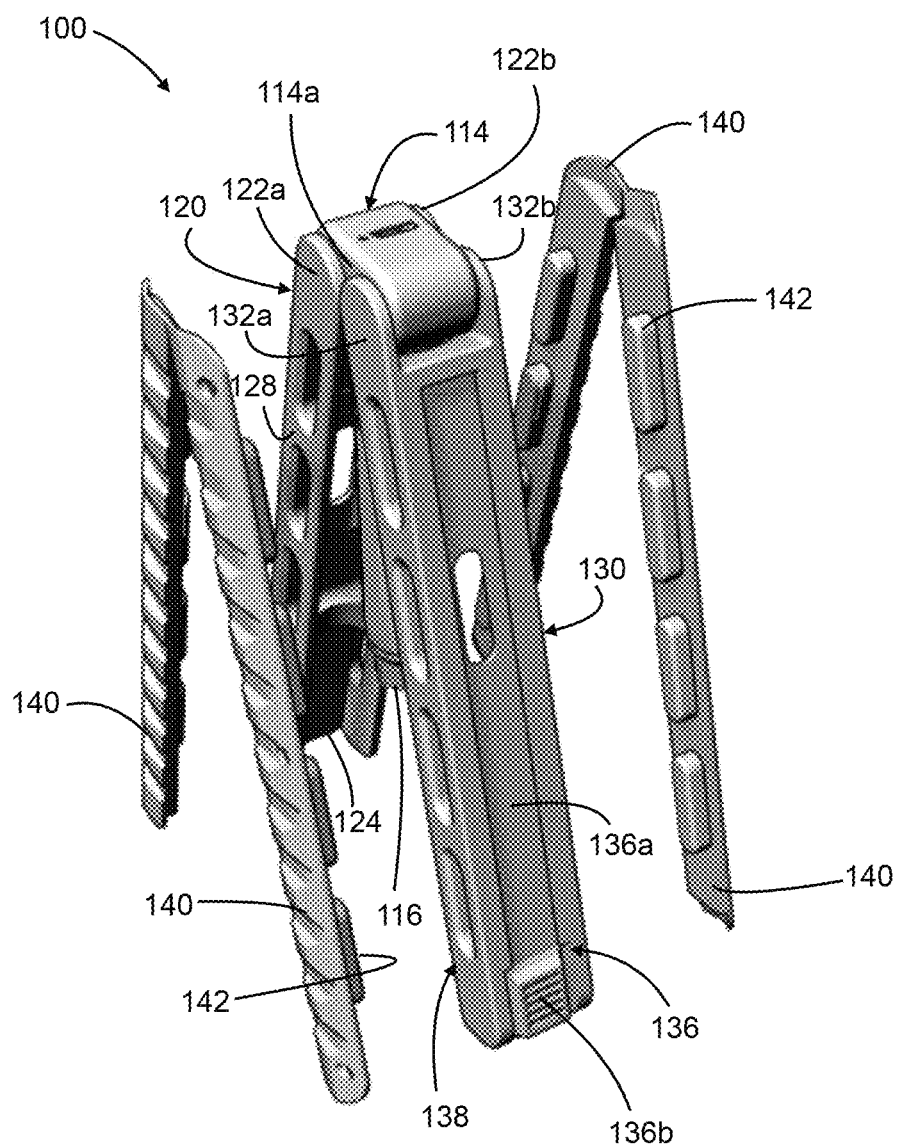
FIG. 4 is a perspective view of the fidget device in an open configuration with faceplates positioned for attachment to the fidget device, according to this disclosure.

The remaining three sides of component grips 120, 130 are configured with component attachment mechanisms for attaching various modular components, such as modular components 160a . . . 160h, to fidget device 100. In one non-limiting example, each component grip includes a side component attachment mechanism, and front and rear component attachment mechanisms. Component grip 130 includes side component attachment mechanism 136 formed on a side of component grip 130 opposite to recess 134 that receives center hub 110 (FIGS. 4 and 5), and front and rear component attachment mechanisms 138 formed on the front and rear edges of side component attachment mechanism 136 (FIGS. 4 and 5). Component grip 120 is formed in like fashion, with a side component attachment mechanism (not shown), and front and rear component attachment mechanisms 128.

The side component attachment mechanism is described with reference to side component attachment mechanism 136 of component grip 130, which description is equally applicable to the side component attachment mechanism (not shown) of component grip 120. In one non-limiting example, side component attachment mechanism 136 comprises component rail 136a, which may be an inverted T-slot or a similarly slotted track. Modular components, such as modular components 160a . . . 160h, include a sliding piece or runner that fits into and slides within component rail 136a, such that the modular component is slidably received on rail 136a. While component rail 136a is described as shaped as a T-slot, it may be formed in other shapes so long as the shape matches the sliding piece or runner on the modular components.

Side component attachment mechanism 136 further comprises retaining mechanism 136b, which can be operated to retain modular components on, or to release modular components from, component rail 136a. In one non-limiting example, retaining mechanism 136b takes the form of a spring-loaded lever configured at an end of component rail 136a opposite from prongs 132a, 132b. Modular components, such as modular components 160a . . . 160h, may be slid over retaining mechanism 136b and onto rail 136a when pressure is applied against retaining mechanism 136b by the modular components. Once the modular components have completely passed over retaining mechanism 136b, it springs back into place to secure the modular components onto rail 136a. To release retaining mechanism 136b, pressure may be exerted on retaining mechanism 136b to push it downward and permit the modular components to be removed from component rail 136a.

Retaining mechanism 136b may take different forms than a spring-loaded lever. For example, retaining mechanism 136b may take the form of a knob that is rotated between a retaining position and a release position. Moreover, some modular components, such as modular component 160h, may attach by interference fit around the sides of component rail 136a rather than fitting within component rail 136a, thereby possibly eliminating the need for a retaining mechanism for such components. Moreover, while the component attachment mechanisms are described herein as taking the form of component rails and retaining mechanisms, component grips 120, 130 may be configured in other ways to retain modular components thereon. For example, the component attachment mechanisms may incorporate a magnet system, a hook-and-loop type system, a breakaway latch, etc. These and other alternative configurations should be understood to be within the scope of this disclosure.

FIGS. 1, 2, 6 and 7 show one configuration of various modular components 160a ... 160h retained in place by the component rails of component grips 120, 130. The modular components allow for different form and function manifestations of fidget device 100, and the selection and configuration of components affect the overall look, playstyle, and weight distribution of fidget device 100. The particular configuration of modular components illustrated and described herein is just one example of limitless possible configurations; the number and form of modular components is entirely up to the user and will likely vary substantially from that illustrated.

Non-limiting examples of modular components that may be attached to fidget device 100 include finger rings for aided skill-based play (e.g., components 160a, 160h) loops, mechanical key switches and keycaps (e.g., components 160d, 160e, 160f), toy knives, lighters, toy chainsaws, rollers, spinning devices, articulating arms, LEDs for glowing night play, dice, joysticks, fidget rollers, keychain connectors for connecting to other devices, electronic sensors, external batteries, control boards, and transition pieces (e.g., components 160b, 160c, 160g) that act as decorative spacers or adapters between other modular components. In one non-limiting embodiment, the modular components may include a chain with a fastening element that attaches around a Pop Socket® that is attached to the back of a mobile computing device. Some modular components may have receiving elements such as their own component rail that allow additional modular components to be attached for further customization.

One type of modular component, finger rings (e.g., modular components 160a, 160h), may be used as aids in skill-based play, and enable a playstyle similar to gun slinging, whereby fidget device 100 is rotated around a user's finger, allowing the user to perform a variety of spinning and catching tricks. Finger rings can be attached at various locations on component grips 120, 130. The location in which a user places the ring in proximity to the center hub pivot point (base 114) will greatly affect the weight distribution, playstyle, and tricks one is able to achieve. For instance, placing a ring closer to the center hub pivot point results in faster spinning capability and is generally easier for catching tricks. Placing a ring further away from the center hub pivot point allows the user to achieve larger spins with greater rotational force but slower overall speed.

Some modular components may incorporate a light source such as a light emitting diode (LED). The light source may illuminate or flash colors when certain events occur, such as if the user is receiving an alert. In some implementations, fidget device 100 and/or the modular components mounted thereon may have a speaker assembly for producing audible sounds and a microphone assembly for transmitting audible sounds.

To accommodate powered modular components, such as light or audio sources, component grips 120, 130 may be configured to deliver power from center hub 110 to powered modular components. In particular, the component rails of component grips 120, 130 may be configured with positive and negative contacts and appropriate conductors to supply power and/or data from center hub 110 to any modular components that require power and/or data to operate.

In addition to the side component attachment mechanisms (component rails), front and rear component attachment mechanisms are also provided. In one non-limiting example, front and rear component attachment mechanisms 138 of component grip 130 take the form of panels 138a with one or more apertures 138b formed therein (FIG. 5). Likewise, front and rear component attachment mechanisms 128 of component grip 120 take the form of panels 128a with one or more apertures 128b formed therein (FIG. 5).

In one non-limiting example, the modular components attached to front and rear component mechanisms 128, 138 comprise faceplates 140. As shown in FIG. 4, faceplates 140 are formed with protrusions 142 that fit within apertures 128b, 138b of front and rear component attachment mechanisms 128, 138 to secure faceplates 140 to component grips 120, 130. Faceplate protrusions 142 may be slightly larger than apertures 128b, 138b that they fit into, such that faceplates 140 are snap-fit and securely held on fidget device 100. Faceplates 140 allow for various aesthetic form factors, grip textures, colors, materials, etc. For example, faceplates 140 may have a gripping surface material or adhesive to prevent slippage between the user's hand and fidget device 100. Faceplates 140 may change the overall look of device 100, as well as its weighting and play style. For instance, some faceplates may contain sleek and minimal features that are better for a faster spinning play style, while other faceplates are more for aesthetic purposes.

FIG. 8 illustrates another embodiment of a fidget device 170 in a single component grip configuration including just one component grip 172, according to this disclosure. Component grip 172 and center hub 175 are formed in the same fashion as center hub 110 and grips 120, 130 of fidget device 100 of FIGS. 1-7, with just one component grip 172 being attached to center hub 175 rather than two component grips 120, 130. As can be seen in FIG. 8, one set of hub sockets 177 is unused since only one component grip 172 is attached to center hub 175. As can be seen in FIG. 8, single component grip device 170 is customizable in like fashion as the dual component grip device, with modular components 176a, 176b, flute endpiece 174, and faceplate 178 being attached.

The many possible configurations of center hub, endpieces, component grips, modular components, and faceplates allows for a wide array of aesthetic and functional manifestations of fidget device 100, affecting the overall look, play style, and weight distribution of the device. Changing these configurations allows the same core product to be marketed to different niche communities depending on the configuration. In this regard, for illustrative purposes, FIGS. 9A and 9B show a small sample of the many possible configurations of center hub, endpieces, component grips, modular components, and faceplates.

Figure 9A:
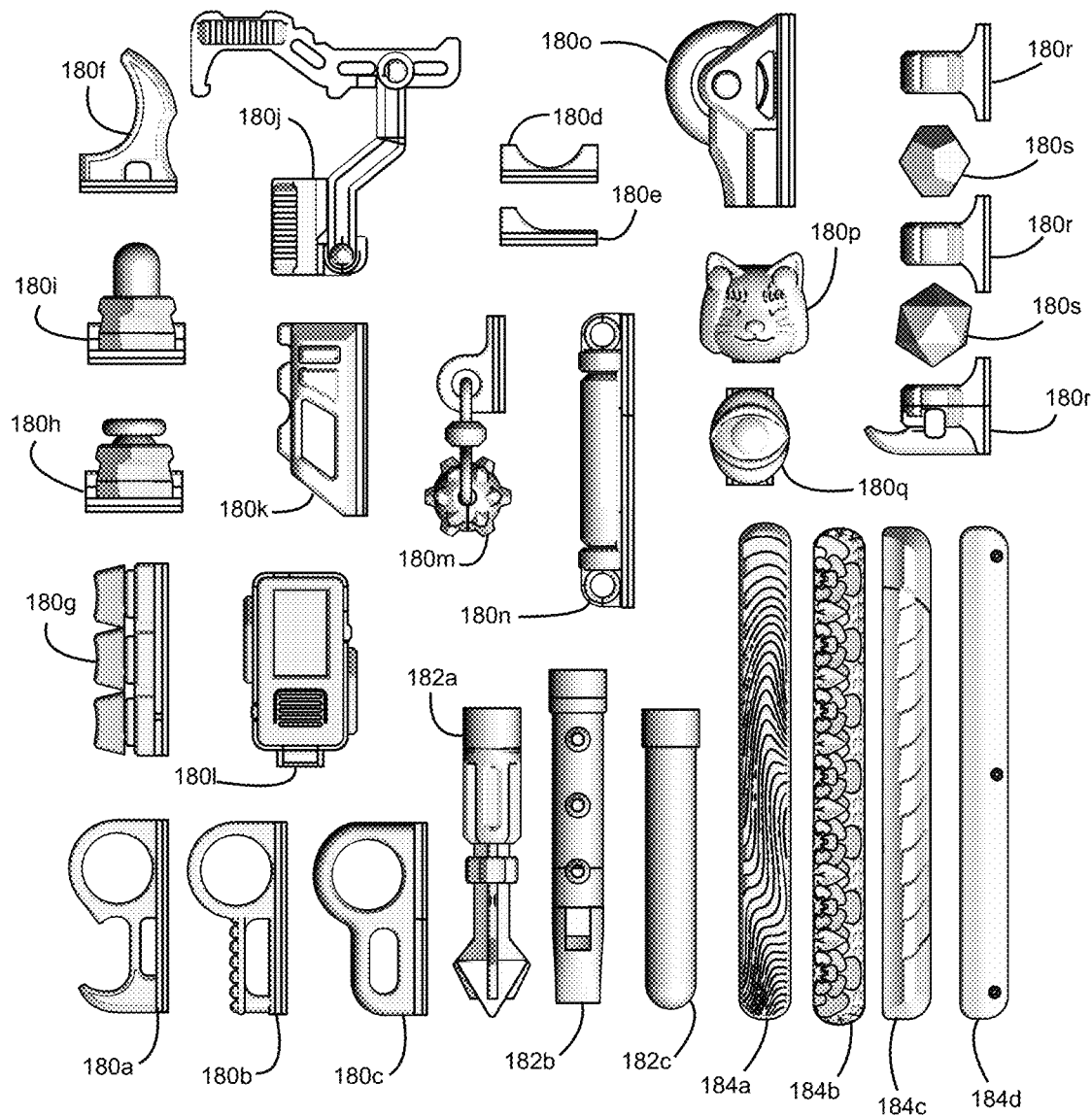
FIG. 9A is a side view of exemplary modular components, endpieces, and faceplates, according to this disclosure.

FIG. 9A shows various modular components 180a ... 180s, endpieces 182a ... 182c, and faceplates 184a ... 184d. FIG. 9A is for non-limiting exemplary purposes only; many other forms and configurations of modular components, endpieces, and faceplates are possible. Components 180a ... 180c are flip rings; components 180d and 180e are spacers; component 180f is a decorative spacer; Component 180g comprises key switches; component 180h is a joystick; component 180i is an LED; component 180j is an articulating accessory arm; component 180k is a decorative reticle; component 180l is a microcontroller; component 180m is a keychain charm; component 180n is a fidget knurl; component 180o is an inline skate wheel for rolling tricks; component 180p is a character charm; component 180q is a decorative eye; components 180r are dice holders; and components 180s are dice. Endpiece 182a is a D4 dice holder; endpiece 182b is a flute; and endpiece 182c is an LED endpiece. Faceplates 184a . . . 184d are various decorative plates which may have various appearances, patterns, colors, and textures.

Figure 9B:
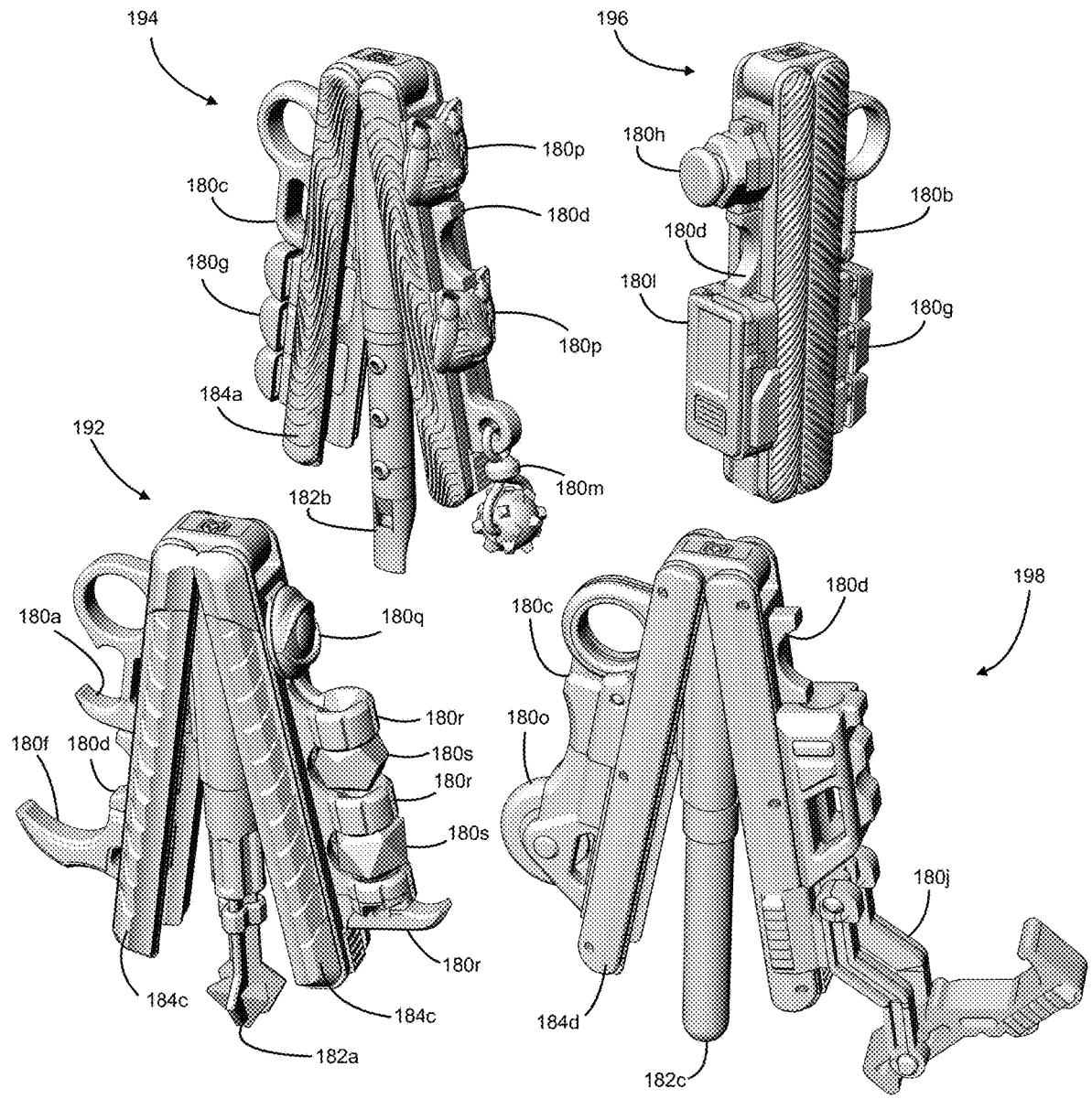
FIG. 9B is a perspective view of exemplary fidget devices configured with various modular components, endpieces, and faceplates, according to this disclosure.

FIG. 9B shows various fidget devices 192 . . . 198 as fully assembled with various modular components, endpieces, and faceplates. FIG. 9b is for non-limiting exemplary purposes only; many other fidget device configurations are possible. Fidget device 192 is a fantasy-styled device assembled with finger ring 180a and spacers 180d, 180f on one component rail; dice holders 180r, polyhedral dice 180s for gameplay such as "Dungeons and Dragons" ("DnD"), and decorative eye 180q on the other component rail; D4 dice holder endpiece 182a on the center hub; and decorative faceplates 184c on the component grips. Fidget device 194 is a cute-styled flute device assembled with finger ring 180c and key switches 180g on one component rail; charm characters 180p, spacer 180d, and keychain charm 180m on the other component rail; flute endpiece 182b on the center hub; and decorative faceplates 184a on the component grips. Fidget device 196 is a gaming-styled device with microcontroller 180l, joystick 180h, and spacer 180d on one component rail; key switches 180g and finger ring 180b on the other component rail; and textured faceplates on the component grips. Fidget device 198 is a science fiction-styled device with inline skate wheel 180o and finger grip 180c on one component rail; articulating accessory arm 180j (which can be configured to resemble a butt stock) and spacer 180d on the other component rail; LED endpiece 182c on the center hub; and decorative faceplates 184d on the component grips.

Fidget device 100 and the modular components to be attached thereto may be made of any appropriate material exhibiting sufficient heat resistance, mechanical strength, and rigidity for continuous playing without degradation or deformation. Non-limiting examples of suitable materials include polycarbonate/acrylonitrile butadiene styrene (PC-ABS), which is a thermoplastic exhibiting high strength, stiffness, heat resistance and impact resistance; polylactic acid (PLA), which is a thermoplastic monomer derived from renewable, organic sources such as corn starch or sugar cane; polyethylene terephthalate glycol (PETG), which is a thermoplastic polyester that delivers significant chemical resistance, formability, and durability; polyamide (nylon); and metal. Fidget device 100 and the modular components to be attached thereto may be formed by any suitable manufacturing process, such as 3-D printing and injection molding.

In one application, fidget device 100 may have one or more sensors and control systems that allow movement of device 100 to be tracked in real time. Fidget device 100 may thereby be used as a video game controller to control the movement of an object in a video game system, or to create and perform a specific move in response to a prompt. The video game system may receive sensor data from sensors on fidget device 100 to assess movement of device 100 with respect to the prompt displayed to the user.

A visual representation in 3D digital space of fidgeting device 100 may also be provided. One or more sensors in device 100 orient and align its 3D position and its visual representation in real-time. The sensors may receive data including (without limitation) movement, video, and audio. This captured data may be sent to a microprocessor that recognizes the captured data (by its size, position, orientation, color, markings, movement sequence, etc.) and then retargets (substitutes/overlays) the last orientation of that image with another digital image in real-time (in one example, at a rate of 10 fps-300 fps) to be displayed on a video screen.

Figure 10:
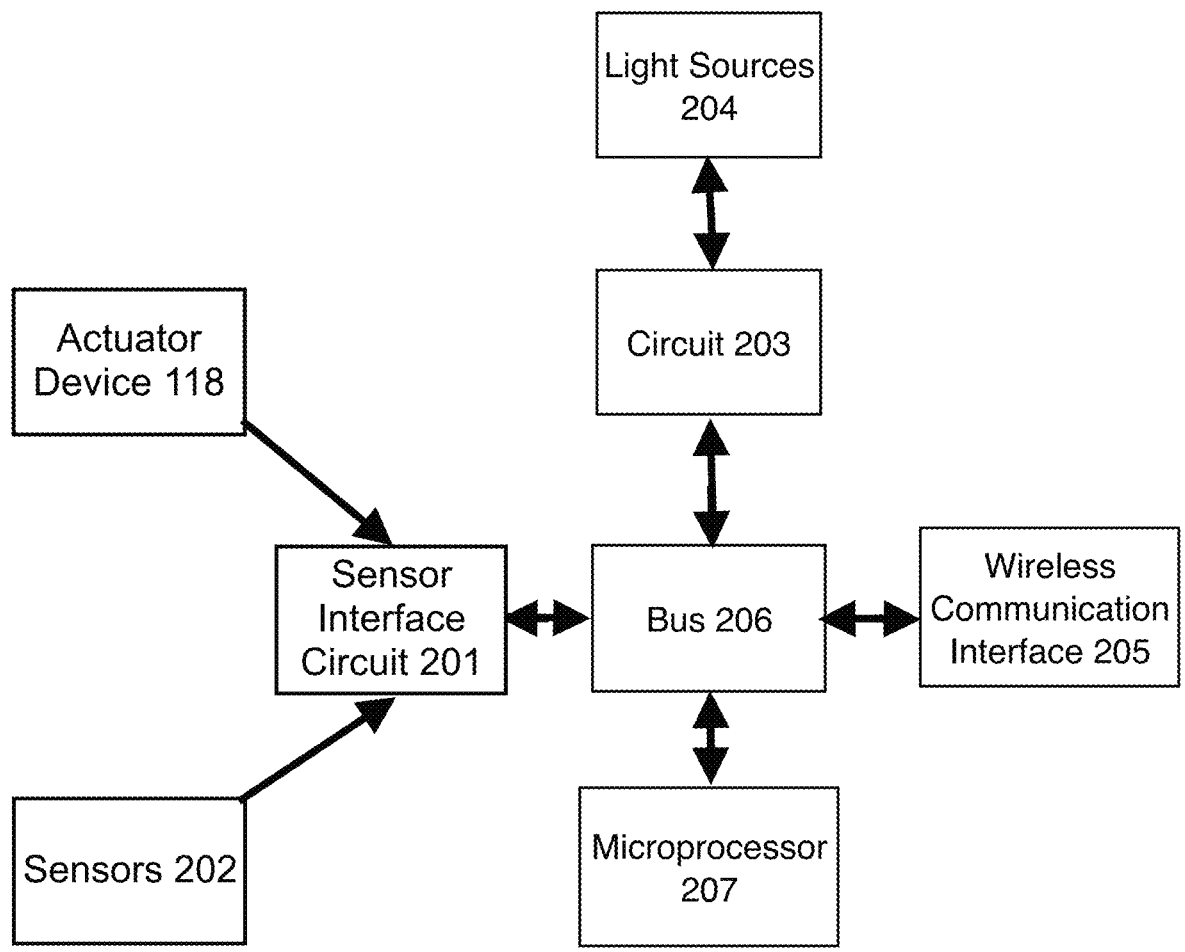
FIG. 10 is a conceptual block diagram of internal circuitry that may be implemented in the fidget device, according to this disclosure.

FIG. 10 is a conceptual block diagram of a control system 200 that may be implemented in fidget device 100 to implement applications such as, without limitation, use as a video game controller or visual representation in 3D digital space of fidget device 100. Control system 200 may include one or more actuation devices 118 such as a button (as previously described), one or more sensors 202, one or more sensor interface circuits 201, light sources 204, circuit 203, wireless communication interface 205, bus 206, and microprocessor 207. These components may be powered by the battery contained in center hub 110 or by another power source to which device 100 is connected.

Sensors 202 may be mounted in or on components of fidget device 100 such as center hub 110, component grips 120, 130, or the modular components mounted on fidget device 100. Examples of sensors 202 include accelerometers, gyroscopes, magnetometers, cameras, pressure sensors, global and local positioning systems, altimeters, and motion sensors. As previously described, some of these sensors may be incorporated in an inertial measurement unit (IMU) contained in center hub 110 or on component rails. Sensors 202 may be on or inside of device 100, a tracking sensor connected to device 100, or may be affixed with adhesive to device 100. Sensors 202 may be used for interactive tracking in skill-based play in which users compete and/or for tracking speed and accuracy of tricks performed, thereby providing a structure and incentive to progress in skill. As previously mentioned, sensors 202 may also be used to provide a visual representation in 3D digital space of fidgeting device 100.

Sensor interface circuit 201 receives signals in the form of voltage or current from sensors 202 and actuation device 118. Microprocessor 207 receives data from sensors 202 and actuation device 118 and generates an appropriate response. Circuit 203 may provide electrical signals, such as voltage, to light sources 204. Wireless communication interface 205 transmits wireless signals indicative of input received from actuation device 118, sensors 202, and/or microprocessor 207 to a computing device such as a video game console, a computer, a wearable device, tablet, mobile computing device, head-mounted display, a computer, a virtual reality system, etc. As previously mentioned, wireless communication interface 205 may comprise an NFC chip. Wireless communication interface 205, microprocessor 207, sensor interface circuit 201, and circuit 203 communicate via bus 206.

Though not illustrated in FIG. 10, fidget device 100 may also comprise one or more vibration motors (e.g., rumble motors, eccentric rotating mass vibration motors) that are selectively actuated by a signal communicated to device 100 via wireless communication interface 205 from another computing device such as a video game console to provide vibration feedback to parts of device 100.

Figure 11:
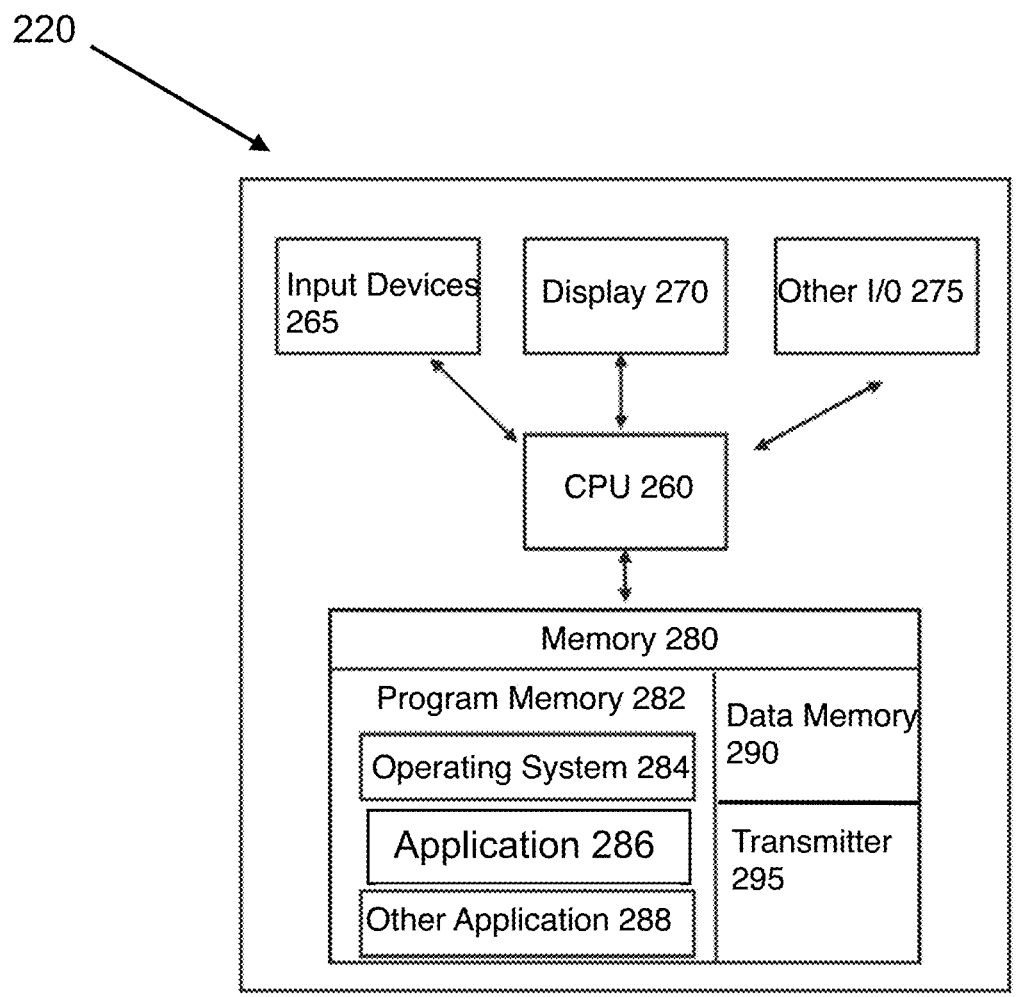
FIG. 11 is a conceptual block diagram of a computing device that the fidget device may communicate with, according to this disclosure.

FIG. 11 is a conceptual block diagram of a computing device 220 that fidget device 100 may communicate with via communication interface 205. Computing device 220 may be, for example, a video game console. Computing device 220 comprises input devices 265, such as a keyboard, mouse, video game controller, etc. that provide user input to a central processing unit (CPU) 260. Input may also be provided by fidget device 100, as described above. Computing device 220 may further comprise a display 270 that provides graphical and textual visual feedback to a user. Display 270 may be a monitor, a head-mounted virtual or augmented reality device, or any other display, and may display movement of a video game object in response to signals received from fidget device 100, or a visual representation in 3D digital space of fidgeting device 100. Other I/O devices 275 may also be coupled to CPU 260.

Computing device 260 further comprises memory 280, which may be implemented as RAM, ROM, a hard drive, a flash drive, etc. Memory 280 may comprise program memory 282 that stores operating system 284, and applications 286 and 288. Memory 280 may also include data memory 290 that stores database query results, configuration data, settings, user preferences, etc. Transmitter 295 may communicate with devices such as fidget device 100, such as by an NFC chip.

Figure 12:
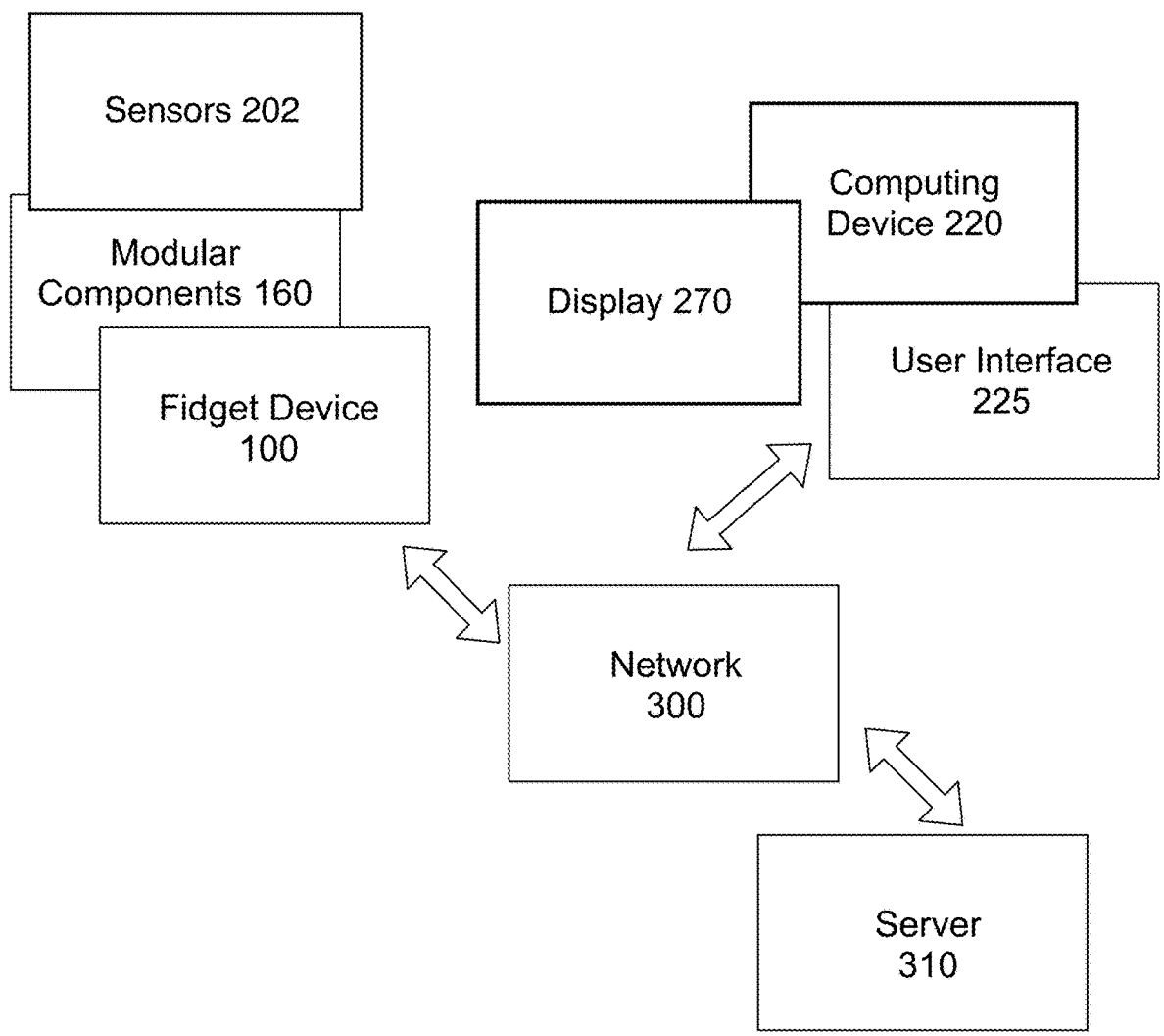
FIG. 12 is a conceptual block diagram of a network environment in which the fidget device and the computing device of FIG. 11 may communicate, according to this disclosure.

FIG. 12 is a conceptual diagram of a network environment in which fidget device 100 and computing device 220 may communicate. As illustrated in FIG. 12, a user may access user interface 225 using computing device 220. Fidget device 100 and computing device 220 may communicate with each other and with a server 330 via network 400. Server 330 may provide various functions and store data related to fidget device 100 and computing device 220.

In this description, drawings, and the following claims, reference is made to various features and aspects of this disclosure. This disclosure includes all possible combinations of such features. Where a feature is disclosed in the context of a particular aspect or embodiment, or a particular claim, that feature can also be used, to the extent possible, in combination with other aspects and embodiments.

Certain terminology used in this description is used for convenience in reference only and is not limiting. For example, words such as "upward," "downward," "left," "right," "front," "rear," "side," "inward," and "outward" refer to directions in the drawings to which reference is made unless otherwise stated. References in the singular tense include the plural, and vice versa, unless otherwise noted.

This disclosure is presented for purposes of illustration and description but is not intended to be exhaustive or limited to the form disclosed. Many modifications and variations will be apparent to those of ordinary skill in the art without departing from the scope and spirit of this disclosure. The embodiments were chosen and described to best explain the principles of this disclosure and its practical applications, and to enable others of ordinary skill in the art to understand the disclosure for various embodiments with various modifications as are suited to the particular use contemplated. The embodiments disclosed herein may be practiced with modification and alteration within the spirit and scope of the appended claims. Thus, this description is illustrative and not restrictive.

The invention claimed is:

1. A fidget device comprising:
a center hub comprising a pivotal attachment mechanism; and
a component grip configured to be pivotally attached to the center hub, the component grip comprising a component attachment mechanism configured to attach one or more modular components to the component grip, wherein the component attachment mechanism comprises:
a component rail configured to slidably receive the one or more modular components; and
a retaining mechanism configured to retain the one or more modular components on the component rail.

2. The fidget device of claim 1, wherein the retaining mechanism comprises a spring-loaded lever.

3. The fidget device of claim 1, wherein the component attachment mechanism comprises one or more apertures configured to receive corresponding protrusions formed on the one or more modular components.

4. The fidget device of claim 3, wherein the one or more modular components comprise faceplates.

5. The fidget device of claim 1, comprising two component grips that are configured to be pivotally attached to the center hub.

6. The fidget device of claim 1, wherein the pivotal attachment mechanism comprises a socket formed in the center hub and configured to receive a corresponding protrusion formed on the component grip.

7. The fidget device of claim 1, wherein the center hub further comprises an endpiece attachment mechanism formed at an end of the center hub opposite from the pivotal attachment mechanism.

8. The fidget device of claim 1, further comprising an actuation device configured to control at least one function of the fidget device.

9. The fidget device of claim 8, wherein the actuation device comprises a button configured to supply power to the fidget device.

10. The fidget device of claim 1, wherein the component grip further comprises a recess that acts as a protective shroud for the center hub.

11. The fidget device of claim 1, wherein the component rail comprises a slotted track.

12. A fidget device comprising:
a center hub comprising a pivotal attachment mechanism; and
a component grip configured to be pivotally attached to the center hub, the component grip comprising a component attachment mechanism configured to attach one or more modular components to the component grip, wherein
the center hub further comprises an endpiece attachment mechanism formed at an end of the center hub opposite from the pivotal attachment mechanism, and
the endpiece attachment mechanism comprises a hub connector with a reduced diameter relative to a remainder of the center hub, the hub connector being configured to retain an endpiece thereon that alters a perceived nature and utility of the fidget device.

13. A fidget device comprising:
a center hub comprising a pivotal attachment mechanism; and
a component grip configured to be pivotally attached to the center hub, the component grip comprising a component attachment mechanism configured to attach one or more modular components to the component grip, wherein
the center hub further comprises an endpiece attachment mechanism formed at an end of the center hub opposite from the pivotal attachment mechanism, and
the center hub is hollow and defines a battery compartment for receiving and holding a battery.

14. The fidget device of claim 13, wherein the endpiece attachment mechanism is configured to provide an electrical connection between the center hub and an endpiece connected to the endpiece attachment mechanism.

15. The fidget device of claim 13, wherein the center hub houses a near field communication (NFC) chip.

16. The fidget device of claim 13, wherein the center hub houses an inertial measurement unit (IMU).

17. The fidget device of claim 13, wherein the component grip is configured with positive and negative contacts and appropriate conductors to supply power and/or data from the center hub to modular components that require power and/or data to operate.

18. A fidget device comprising:
a center hub comprising a pivotal attachment mechanism;
a component grip configured to be pivotally attached to the center hub, the component grip comprising a component attachment mechanism configured to attach one or more modular components to the component grip; and
a sensor that allows movement of the fidget device to be tracked in real time.

19. The fidget device of claim 18, wherein the sensor orients a 3D position of the fidget device to enable a visual representation in 3D digital space of the fidget device.

* * * * *